US006656166B2

(12) United States Patent
Lurie et al.

(10) Patent No.: US 6,656,166 B2
(45) Date of Patent: Dec. 2, 2003

(54) GUIDING INTRODUCER FOR INTRODUCING MEDICAL DEVICES INTO THE CORONARY SINUS AND PROCESS FOR USING SAME

(75) Inventors: Keith G. Lurie, Minneapolis, MN (US); Jean Jacques Blanc, Brest Cedex (FR); David G. Benditt, Minneapolis, MN (US); Daniel J. Starks, Minnetonka, MN (US)

(73) Assignee: St. Jude Medical, Minnetonka, MN (US)

( * ) Notice: Subject to any disclaimer, the term of this patent is extended or adjusted under 35 U.S.C. 154(b) by 0 days.

(21) Appl. No.: 09/930,315

(22) Filed: Aug. 15, 2001

(65) Prior Publication Data

US 2002/0029030 A1 Mar. 7, 2002

Related U.S. Application Data

(62) Division of application No. 08/853,631, filed on May 9, 1997, now Pat. No. 6,277,107, which is a continuation-in-part of application No. 08/625,908, filed on Apr. 1, 1996, now Pat. No. 5,722,963, which is a continuation of application No. 08/371,849, filed on Jan. 12, 1995, now Pat. No. 5,549,581, which is a continuation of application No. 08/106,383, filed on Aug. 13, 1993, now Pat. No. 5,423,772.

(51) Int. Cl.$^7$ .............................................. A61M 5/00
(52) U.S. Cl. ..................... 604/264; 604/104; 604/523; 604/532; 607/9
(58) Field of Search .................. 128/898; 606/128, 606/108, 191–200; 623/1.11, 1.26, 2.11, 11.11; 604/19, 96.01–109, 164.01, 164.02–164.11, 164.13, 170.02, 170.03, 171, 264, 523, 532, 913, 507–510, 158, 160, 161, 528–531, 28, 500; 600/585, 372–397, 433–435, 466, 467, 481, 508–528; 607/9, 28

(56) References Cited

U.S. PATENT DOCUMENTS

| 4,166,469 A |   | 9/1979  | Littleford |
|-------------|---|---------|------------|
| 4,243,050 A | * | 1/1981  | Littleford ..................... 607/122 |
| 4,488,561 A | * | 12/1984 | Doring ......................... 607/125 |
| 4,569,347 A |   | 2/1986  | Frisbie |
| 4,801,297 A |   | 1/1989  | Mueller |
| 4,983,168 A | * | 1/1991  | Moorehead .................. 604/523 |
| 5,171,232 A |   | 12/1992 | Castillo et al. |
| 5,195,990 A |   | 3/1993  | Weldon |
| 5,203,776 A |   | 4/1993  | Durfee |
| 5,312,355 A | * | 5/1994  | Lee ............................ 604/160 |
| 5,322,509 A |   | 6/1994  | Rickerd |
| 5,409,469 A | * | 4/1995  | Schaerf ....................... 604/524 |
| 5,423,772 A | * | 6/1995  | Lurie et al. .................. 604/525 |
| 5,488,960 A | * | 2/1996  | Toner .......................... 600/585 |
| 5,549,581 A |   | 8/1996  | Lurie et al. |
| 5,643,231 A |   | 7/1997  | Lurie et al. |
| 6,277,107 B1 |  | 8/2001  | Lurie et al. |

* cited by examiner

*Primary Examiner*—Glenn K. Dawson
(74) *Attorney, Agent, or Firm*—Scott R. Cox

(57) ABSTRACT

A coronary sinus guiding introducer utilized to introduce medical devices, such as electrode leads, into the coronary sinus of a human heart. This guiding introducer contains a precurved distal portion, which curves through an arc of about 50 to 150 degrees. Preferably, the distal portion contains a pair of generally coplanar curves, wherein the arc of the first curve is from about 20 to about 60 degrees and the arc of the second curve is from about 30 to about 90 degrees and wherein the second curve is generally coplanar with the first curve. In an alternative embodiment, the second curve curves out of a plane formed by the first curve from about 15 to about 90 degrees. In addition, preferably the guiding introducer is splittable. Also disclosed is a process for introducing medical devices through the lumen of the precurved, coronary sinus guiding introducer.

19 Claims, 10 Drawing Sheets

GUIDING INTRODUCER FOR INTRODUCING MEDICAL DEVICES INTO THE CORONARY SINUS AND PROCESS FOR USING SAME

RELATES BACK

This application is a divisional of application Ser. No. 08/853,631, filed May 9, 1997, now U.S. Pat. No. 6,277,107, which is a continuation-in-part of application Ser. No. 08/625,908, filed Apr. 1, 1996, now U.S. Pat. No. 5,722,963, which is a continuation application of Ser. No. 08/371,849, filed Jan. 12, 1995, now U.S. Pat. No. 5,549,581, which is a continuation application of Ser. No. 08/106,383, filed Aug. 13, 1993, now U.S. Pat. No. 5,423,772.

FIELD OF INVENTION

This invention relates to sheaths and introducers which are utilized in a human heart. More particularly, this invention relates to a precurved, guiding introducer for introducing specialized medical devices into the coronary sinus and a process for introduction of those devices into the coronary sinus utilizing the precurved, guiding introducer.

BACKGROUND OF INVENTION

Many medical procedures require the introduction of specialized medical devices into the human heart. For example, electrical leads, such as pacemaker leads, defibrillation leads or leads used for cardioversion, and shunts or specialized catheters are frequently placed at specific locations within the heart to perform specialized cardiac procedures. Many of these medical devices, such as pacemaker leads, are very pliant and flexible. This flexibility is necessary to prevent damage, particularly to the patient's vasculature, during the period of time those products are present in the patient. However, because of this flexibility, it is quite difficult to advance these devices through the patient's vasculature into the heart without the use of some stiffening element with the device. For example, one method of stiffening certain medical devices is to introduce a stylet into the lumen of the medical device.

The typical procedure for introducing these devices into the heart requires passage through the patient's vasculature. One early approach to introduction of devices into the vasculature was to surgically cut an opening into the patient's vasculature. However, there are several disadvantages to this procedure. To address these disadvantages, percutaneous methods have been developed to create openings in the vasculature. Once an opening is created, frequently by use of a hollow needle, a dilator is usually inserted into the vasculature which gradually increases the size of the opening. The dilator has a tapered end which spreads apart the tissue at the puncture sight as it is advanced through the vasculature. Often the dilator will contain a lumen through which other medical devices may also be inserted into the vasculature.

As an example, in a typical procedure for introduction of an electrode lead into the heart, a guidewire is first introduced through the vasculature into the appropriate chamber of the heart. This process is disclosed, for example, in U.S. Pat. No. 5,488,960. With the guidewire in place, a catheter/introducer or dilator/introducer combination is then passed over the guidewire and directed into the patient's body. The catheter or dilator is then removed from the introducer. The introducer then provides a platform from which the lead may be introduced into the heart, frequently with a stylet placed within the lumen of the lead to assist in stiffening the structure of the lead and also to permit precise placement of the device within the heart.

With conventional introducers, the maximum diameter of the pacemaker lead that can be inserted is no larger than the lumen of the introducer. This limitation created a significant problem because of the nature of pacemaker leads. Frequently, the pacemaker lead's proximal end contained an electrical connector for connection to the pulse generator. Because the size of the connecter is often larger than the diameter of the lumen of conventional cardiac introducers, splittable sheaths have been designed to assist in the insertion of these electrode leads. See, for example, U.S. Pat. Nos. 4,983,168, 4,243,050 and 4,166,469. Once the introducer directs the placement of the medical device, such as an electrode lead, into the body, the splittable introducer is torn apart lengthwise as it is withdrawn from the body. By being splittable, the size of the lumen of the splittable introducer can remain relatively small as it need be no larger than is necessary for passage of the distal tip of the medical device through the lumen of the introducer. In addition, U.S. Pat. No. 5,312,355 discloses a splittable hemostatic valve that is utilized in combination with a splittable sheath for introduction of a pacemaker electrode into a patient.

While specialized medical devices are utilized throughout the human body, many have been used in the heart, in general and specifically in the coronary sinus. The coronary sinus is the largest cardiac vein in the heart and serves as a venous conduit from smaller veins within the myocardium to the right atrium. A tissue fold or primitive valve covers the coronary sinus ostium to prevent blood from backflowing into the coronary sinus as it is being pumped out of the right atrium. Located within the right atrium, generally, above the coronary sinus is an oval depression called the fossa ovalis. Between the inferior vena cava and the coronary sinus ostium is the eustaclan ridge. The location of each of these elements may vary from patient to patient.

The coronary sinus is often used for electrophysiological procedures in the heart, including both diagnostic and treatment procedures. The coronary sinus can also be used as a location for pacing both the left and right sides of the heart. Gaining access to the ostium of the coronary sinus is a very difficult procedure, especially because of the large number of similar anatomical structures located near the coronary sinus within the right atrium. It is especially difficult because these anatomical structures do not show up on a fluoroscope.

Current procedures available for introduction of devices such as pacemakers, implantable defibrillators, specialized catheters or devices used for cardioversion into the coronary sinus are frequently time consuming and difficult. To address this problem for a particular type of diagnostic catheter, U.S. Pat. Nos. 5,423,772 and 5,549,581 disclose a precurved, coronary sinus catheter, which because of its curvature, can be advanced through the patient's vasculature directly into the coronary sinus where it can be used for diagnostic and treatment procedures. U.S. Pat. No. 5,488,960 discloses a different type of device designed for use in the coronary sinus.

Accordingly, it is an aspect of this invention to disclose a device which assists in the efficient placement of medical devices particularly small, flexible medical devices, such as electrode leads, into the coronary sinus.

It is a further aspect of this invention to disclose an introducer for introducing a medical device, such as a flexible lead for use with a pacemaker, defibrillator or for cardioversion, into the coronary sinus.

Another aspect of this invention is to disclose a fixed shape introducer to be used for the introduction of medical devices into the coronary sinus.

Another aspect of the invention is to disclose a fixed shaped introducer which can be used in a process for the introduction of medical devices into the coronary sinus without using a guidewire.

Another aspect of the invention is to disclose a process for the introduction of flexible medical devices into the coronary sinus of the human heart using a precurved guiding introducer.

These and other aspects are obtained by the design of the device of the present invention and by the process disclosed herein.

SUMMARY OF INVENTION

The present invention relates to a coronary sinus introducer utilized to introduce a medical device, such as a lead for use with a pacemaker, defibrillator or for cardioversion into the coronary sinus of the heart. This introducer is designed with a predetermined, fixed curve in its distal section which curves through an arc of from about 50 to 150 degrees. Preferably the distal curved section comprises a pair of separate, generally coplanar curves, with the arc of the first curve from about 20 to about 60 degrees and the arc of the second curve from about 30 to about 90 degrees. In addition, this fixed curve coronary sinus introducer is preferably splittable so that after introduction of the medical device into the coronary sinus, the introducer may be split into two pieces as it is withdrawn from the patient.

The invention also encompasses a process for introducing a medical device, such as a lead for a pacemaker, defibrillator or for cardioversion, into the coronary sinus of the human heart. During the process a stiffening element is introduced into the lumen of the precurved, coronary sinus introducer. The coronary sinus introducer with the stiffening element is directed through the vasculature of the human body into the right atrium of the human heart and then into the coronary sinus. The stiffening element is then removed from the lumen of the coronary sinus introducer. The medical device for use in the coronary sinus is introduced into the lumen of the coronary sinus introducer, and the medical device is advanced through the lumen of the coronary sinus introducer, into the coronary sinus. The introducer is withdrawn from the heart over the medical device while the medical device is retained in the coronary sinus of the heart.

The coronary sinus introducer is not limited to introducing different types of leads into the coronary sinus. The invention also encompasses an introducer for introducing any small medical device into the heart as well as electrophysiological diagnostic devices, such as are used for sensing and ablation procedures.

BRIEF DESCRIPTION OF THE DRAWINGS

FIG. 2a is a side view of the coronary sinus guiding introducer used with a superior approach to the right atrium.

FIG. 2b is a side view of the coronary sinus guiding introducer of FIG. 2a rotated 90 degrees from the position of FIG. 2a.

FIG. 7b is a side view of the coronary sinus guiding introducer of FIG. 7a rotated 90 degrees from its position in FIG. 7a.

FIG. 8a is a side view of a precurved dilator for use with the guiding introducer as shown in FIGS. 2a, 2b and 2c used for a superior approach to the coronary sinus.

FIG. 8b is a side view of the precurved dilator of FIG. 8a rotated 90 degrees from its position in FIG. 8a.

FIG. 8c is an end view of the precurved dilator of FIG. 8a viewed from its distal end.

FIG. 11a is a side view of a precurved dilator for use with the guiding introducer shown in FIGS. 7a, 7b and 7c used for an inferior approach to the coronary sinus.

FIG. 11b is a side view of the precurved dilator of FIG. 11a rotated 90 degrees from its position in FIG. 11a.

FIG. 11c is an end view of the precurved dilator of FIG. 11a viewed from its distal end.

FIG. 12a is a side view of a precurved dilator preferably for use with the guiding introducer of FIG. 5.

FIG. 12b is a side view of the dilator of FIG. 12a rotated 90 degrees from its position in FIG. 12a.

DETAILED DESCRIPTION OF THE DRAWINGS

Figure 1A:
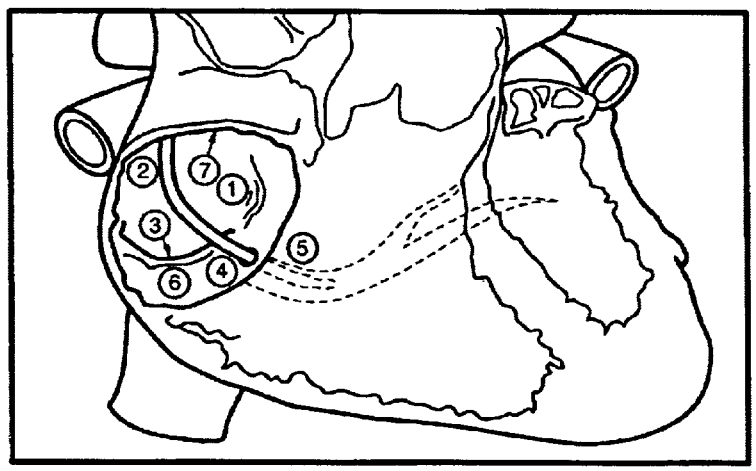
FIG. 1a is a cutaway view of the human heart from the right side showing the coronary sinus guiding introducer placed in the coronary sinus using the superior approach.

The coronary sinus guiding introducer of the present invention assists in the introduction of specialized medical devices, such as a pacemaker lead or defibrillator lead, into the coronary sinus of the human heart. The coronary sinus is the largest cardiac vein and serves as a conduit for access to various locations within the heart. Depending on the depth of insertion of the medical device into the coronary sinus, both the left and right atria and the left and right ventricles of the heart can be analyzed. However, introduction of a medical device into the ostium of the coronary sinus is quite difficult as a result of the structure of the heart, the difficulty in locating the coronary sinus using conventional medical technology and the constantly changing shape of the heart while beating. Because of its unique shape, the introducer of the present invention assists in rapid placement of medical devices within the coronary sinus, thereby reducing the amount of time necessary for performance of the medical procedure. (The term "introducer" is synonymous with the term "sheath.")

Two approaches are commonly used for placement of a medical device within the coronary sinus, an inferior approach from below the heart, and a superior approach from above the heart. In the superior approach, the device is advanced through either the internal jugular or subclavian vein through the superior vena cava into the right atrium until it is directed toward the coronary sinus. See FIG. 1a. In the inferior approach, the device is generally advanced through the femoral vein through the inferior vena cava into the right atrium. See FIG. 1b. The tip of the device is then directed toward the ostium of the coronary sinus. The superior approach is the preferred approach.

Medical practitioners often monitor the introduction of medical devices and their progress through the vascular system by use of fluoroscopes. Unfortunately, fluoroscopes cannot easily identify specific features in the heart, in general, and the critically important structures of the right atrium, specifically, thus making placement of medical devices into the coronary sinus extremely difficult. In addition, placement of medical devices in the coronary sinus is especially difficult when the heart is beating. In particular, when the medical device to be introduced is a flexible, flaccid product such as a pacemaker lead, placement in the coronary sinus is especially difficult.

The structure and shape of the guiding introducer of the present invention addresses and solves this problem and permits the precise placement necessary for introduction of medical devices, such as leads, into the coronary sinus. The shaped guiding introducer of this invention readily positions the medical device inserted through its lumen at the precise location necessary for the procedure as a result of its shape.

This specially designed guiding introducer is generally produced from a conventional elongated introducer. While the guiding introducer of the invention is described as having two sections, it is produced utilizing a conventional introducer production procedure and is preferably formed as a single, unitary structure. Features of this guiding introducer include its unique shape, splittable structure, increased stiffness to minimize compression when positioned in tight bends, radiopaque tip markers, and vents, which will be discussed in more detail later.

Figure 2C:
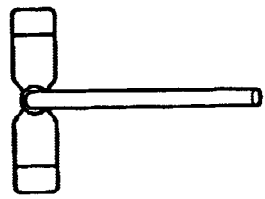
FIG. 2c is an end view of the coronary sinus guiding introducer of FIG. 2a viewed from its distal end.
Figures 2A, 2B:
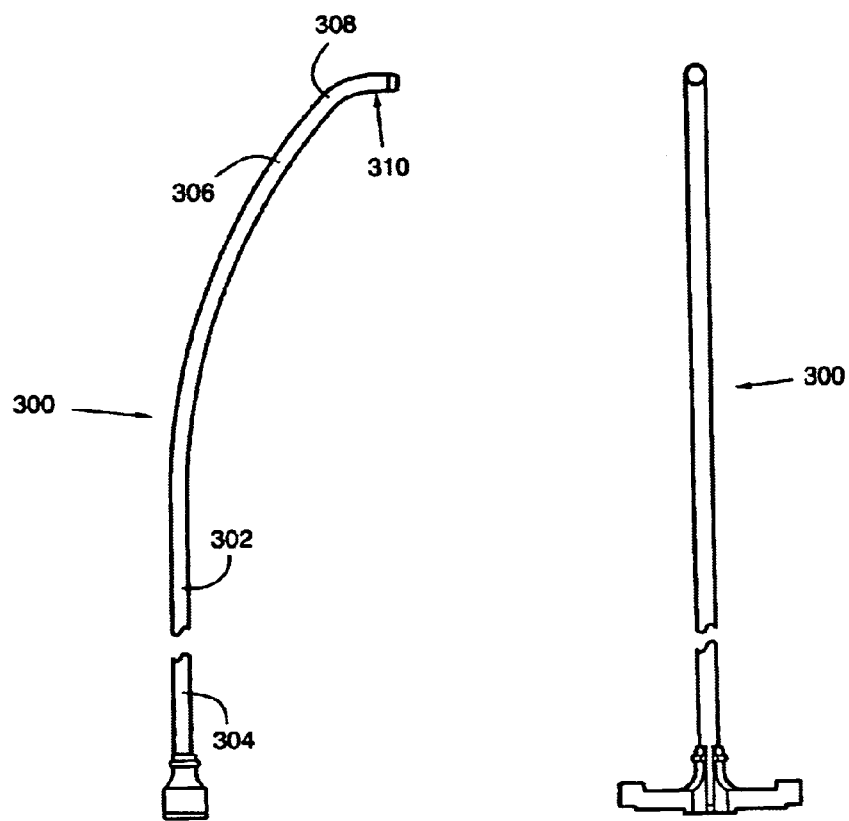

As shown in FIGS. 2a, 2b and 2c, the coronary sinus guiding introducer (300) for use in a superior approach to the right atrium has a distal section (302) and a proximal section (304). The overall length of the introducer (300) can range from about 12 inches (30 cm) to about 50 inches (120 cm), depending upon the size and age of the patient and whether the superior or inferior approach is chosen for insertion of the medical device. The proximal section (304) of this guiding introducer is a conventional, generally elongated, hollow, generally straight introducer section of sufficient length for introduction into the patient and for manipulation from the point of insertion to the right atrium of the heart.

Figures 3, 4:
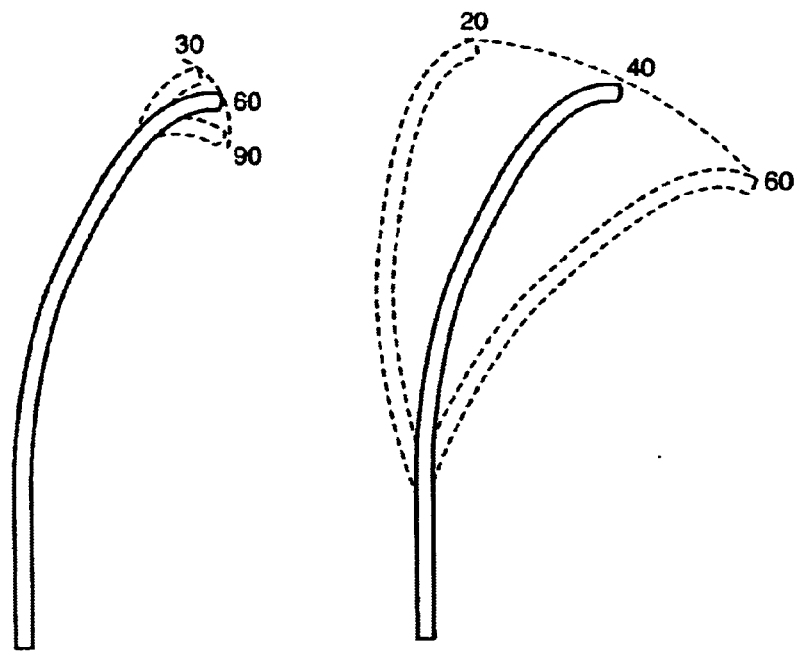
FIG. 3 is a side view of the coronary sinus guiding introducer used for a superior approach showing the acceptable range of curves for the first curve of the distal section.
FIG. 4 is a side view of the coronary sinus guiding introducer used for a superior approach showing the acceptable range of curves for the second curve of the distal section.

Merged with the distal end of the proximal section (304) of this guiding introducer (300) is the second, precurved distal section (302), as shown in FIG. 2a. In a preferred embodiment for use when the superior approach is chosen, the precurved distal section (302) is comprised of two separate curves, although more than two curves are within the contemplation of this invention. In a preferred embodiment the first curve (306) curves through an arc of about 20 to about 60 degrees, preferably from about 30 to about 50 degrees and most preferably from about 35 to about 45 degrees (see FIG. 3) with a radius from about 2.0 inches (5.1 cm) to about 5.0 inches (12.7 cm), preferably from about 3.0 (7.6 cm) to about 4.0 inches (10.2 cm). At the distal end of this first curve is a second curve (308) which forms a canted tip (310) for the guiding introducer. This second curve (308) curves through an arc from about 30 to about 90 degrees, preferably from about 45 to about 90 degrees, and most preferably from about 50 to about 70 degrees (see FIG. 4), with a radius of the arc from about 0.2 (0.5 cm) to about 2.0 inches (5.1 cm), and preferably from about 0.2 (0.5 cm) to about 1.0 inch (2.6 cm). Alternatively, the curves of the distal section can be modified such that the sum of the arcs of the first curve (306) and the second curve (308) is from about 50 to about 150 degrees, preferably about 85 to about 115 degrees. In a preferred embodiment, the second curve (308) is an extension of the first curve (306) curving in the same general direction as the first curve (306) resulting in the first and second curves (306, 308) being substantially coplanar (within about 15 degrees of coplanar), though minor variations outside of a plane formed by the first curve are certainly within the contemplation of the invention.

Figure 5:
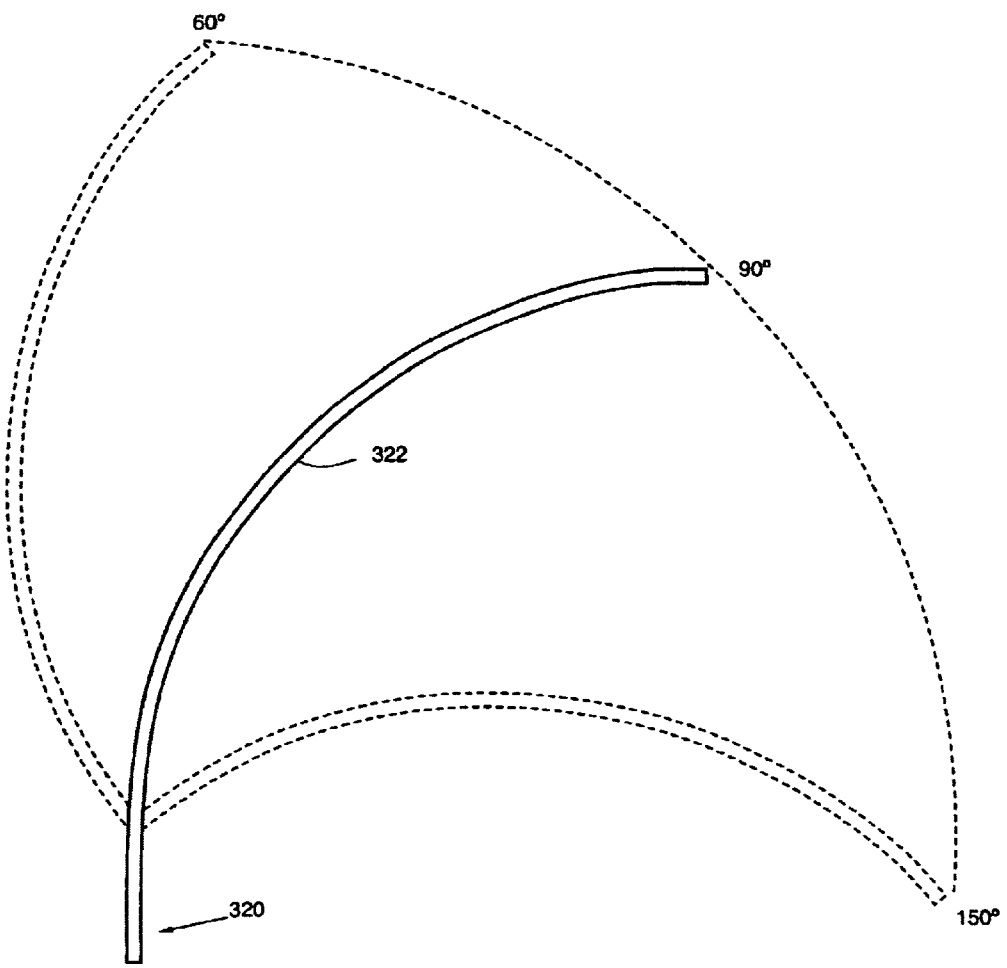
FIG. 5 is a side view of the coronary sinus guiding introducer used for a superior approach showing the acceptable range of curves for the distal section of the guiding introducer, wherein the first and second curves are combined into a single curve.

In an alternate preferred embodiment of the guiding introducer (320) shown in FIG. 5, the first and second curves are combined in a single curve (322) whose arc is between about 50 and about 150 degrees, preferably from about 75 to about 140 degrees, and most preferably 85 degrees to about 115 degrees, with a radius of about 2.0 (5.1 cm) to about 6.0 inches (15.3 cm), preferably about 3.0 (7.6 cm) to about 5.0 inches (12.7 cm). In this alternative preferred embodiment, the first and second curves from the earlier embodiment are combined into a single curve (322).

Figure 6:
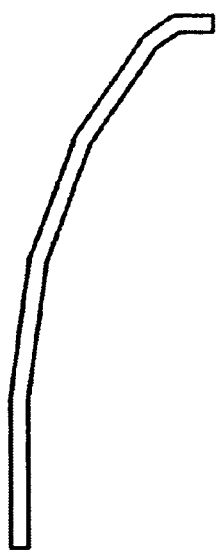
FIG. 6 is a side view of an alternative embodiment of the coronary sinus guiding introducer used for a superior approach showing one combination of curved and straight sections of the distal section of the guiding introducer.

As a further alternative embodiment of the guiding introducer (330) shown in FIG. 6, any combination of curves or curved and straight sections is acceptable which results in an overall shape for the distal section of the guiding introducer which is similar to the shapes of the embodiments earlier described and which causes the distal tip (332) or canted tip of the guiding introducer to enter the coronary sinus after introduction into the right atrium. This combination includes curved and straight portions that are coplanar.

Figure 7C:
FIG. 7c is an end view of the coronary sinus guiding introducer of FIG. 7a viewed from its distal end.
Figure 7A:
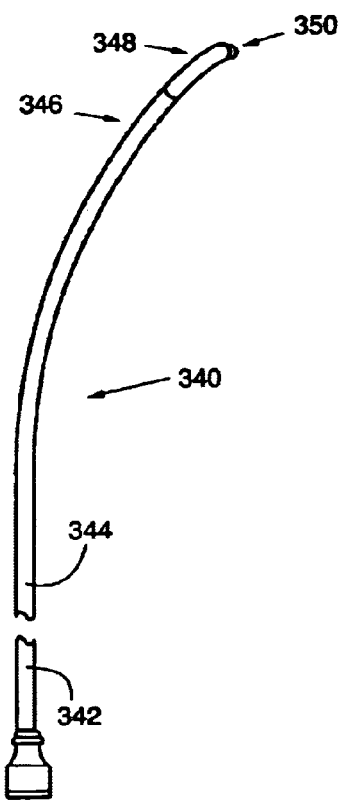
FIG. 7a is a side view of an alternate preferred embodiment of the coronary sinus guiding introducer designed for an inferior approach to the right atrium.
Figure 7B:
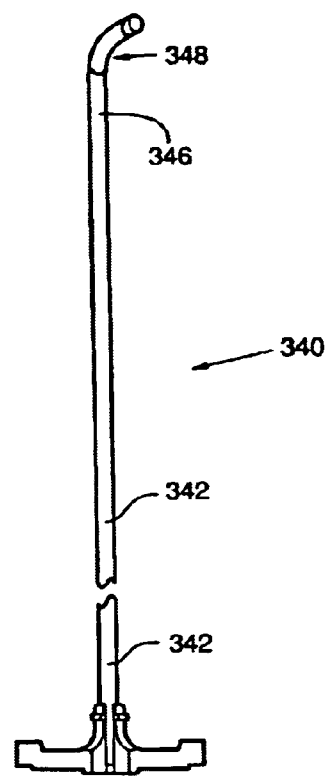

In a further preferred embodiment of the guiding introducer (340) shown in FIGS. 7a, 7b and 7c, when an inferior approach to the coronary sinus is utilized for introducing the coronary sinus guiding introducer into the heart, a different preferred shape of the distal end of the guiding introducer is utilized. In addition, the guiding introducer (340), as a whole and specifically the first proximal section (342) of the device, are preferably longer than the length of the coronary sinus guiding introducer (300) of the first preferred embodiment shown in FIGS. 2a, 2b and 2c. In this further preferred embodiment of FIGS. 7a, 7b and 7c, the first curve (346) of the distal section (344) shown in FIG. 7a is substantially similar to the first curve (306) of FIG. 2a of the first preferred embodiment of FIG. 2a. The second curve (348) or canted tip of FIG. 7a, however, in addition to curving through an arc of about 30 to about 90 degrees, preferably from about 30 to about 50 degrees, and most preferably about 50 to about 70 degrees, with a radius of the arc from about 0.2 (0.5 cm) to about 2.0 inches (5.1 cm), preferably from about 0.2 (0.5 cm) to about 1.0 inches (2.6 cm), also curves out of a plane formed by the first curve (346) in an amount from about 15 to about 90 degrees, and preferably from about 30 to about 75 degrees as shown in FIG. 7b. This out-of-plane curve permits easier placement of the distal tip (350) of the introducer (340) into the coronary sinus when an inferior approach is utilized than is permitted by the design of the first preferred embodiment of FIGS. 2a, 2b and 2c. Again, as with the first preferred embodiment, the first and second curves (346, 348) may be combined in any manner which results in the same general shape for the guiding introducer and which directs the distal tip (350) of the guiding introducer (340) into the coronary sinus after introduction into the right atrium. These combinations may also include any combination of curved or straight sections which when combined result in the same general, overall shape of the distal section of the coronary sinus guiding introducer (340) of this alternative embodiment.

The distal canted tip of the guiding introducer may be, and preferably will be, tapered to form a good transition with a dilator. This tapering is preferably less than 10 degrees, and more preferably, about 4 degrees to about 7 degrees. The guiding introducer preferably may also contain one or a multitude of radiopaque tip marker bands near the distal tip of the guiding introducer or it may be radiopaque throughout its entire length. This can be accomplished by utilizing material additives, such as barium sulfate. This guiding introducer may also contain one or a plurality of vents near its distal tip. However, in a preferred embodiment, no vents are utilized in the device. If vents are used at all, they should be located no more than about one inch from the distal tip of the guiding introducer and preferably from about 0.1 to about 1.0 inch from the tip.

The guiding introducer may be made of any biocompatible material suitable for use in humans which has a memory or permits distortion from and substantial return to the desired three dimensional shape, such as polyethylene or polyurethane. In a preferred embodiment, the distal tip of the guiding introducer may be made of a more pliable, more compressible material, than the remaining length of the coronary sinus guiding introducer to prevent damage to the vasculature and the coronary sinus when in use. Also, preferably, the distal tip is made radiopaque.

For the purpose of illustration and not limitation, the internal diameter of the guiding introducer may vary from about 4 to about 16 French (1 French equals ⅓ of a millimeter). Such guiding introducers can thus accept dilators whose outside diameter is from about 4 to about 16 French. Obviously, if larger or smaller dilators or other medical devices are used in combination with the guiding introducer, modifications in size and shape of the guiding introducer can be made. The precurved guiding introducer of the invention may also be multi-lumened. In another alternative embodiment, the structure of the introducers may be modified to permit the presence of an inflatable balloon near or at its distal tip or electrodes for sensing or ablation.

Variations in size and shape of the guiding introducer are intended to encompass pediatric uses for the guiding introducer of the present invention, although the preferred uses are in adult human hearts. It is well recognized that pediatric uses may require reductions in size of the various sections of the guiding introducer, in particular shortening the first section, but without any significant modification to the shape or curvature of the distal section of the guiding introducer. In addition, variations in size or shape are also intended to encompass specialized situations that sometimes occur in patients with enlarged or rotated hearts.

The structure of the guiding introducer should be stiff enough to prevent substantial movement of the distal section of the guiding introducer once in place within the heart and to retain its general shape. In order to permit good torque control, the generally straight section may be made stiffer than the curved distal section. This stiffer construction can be achieved by conventional construction techniques, such as increasing the thickness of the material or manufacturing a portion of the guiding introducer from a material possessing characteristics of enhanced stiffness, such as by adding a metal component, a stiffener material or by fusing different materials together.

In a preferred embodiment the entire length of the guiding introducer is splittable to permit the guiding introducer to be divided into two separate halves as it is removed from the patient's body. Any structure which will permit the division of the guiding introducer into two separate longitudinal halves is within the scope of the invention. In a preferred embodiment, the guiding introducer contains a pair of mechanically formed, longitudinally extending zones of reduced thickness defined by internally scored, longitudinally shallow grooves or indentations running throughout the length of the introducer. These mechanically formed, reduced thickness zones permit the guiding introducer to be "split" following use. Alternatively, if the lumen of the guiding introducer is sufficiently large and the size of the diameter of the medical device passing through the guiding introducer is not larger than the lumen of the guiding introducer, it is not necessary that the guiding introducer be splittable.

The second, distal section of the guiding introducer should be stiff, but flexible. This will permit the curved distal section to be straightened when a dilator is passed through its lumen to facilitate insertion into the patient's vasculature and for passage through the vasculature into the right atrium. In a preferred embodiment, the distal tip should be more pliable than the remaining portions of the guiding introducer to prevent damage to the vasculature during insertion of the guiding introducer through the vasculature.

The stiffness of the coronary sinus guiding introducer can also be enhanced by insertion of a dilator or shaped catheter within the lumen of the guiding introducer. A "dilator" is an inner strengthening element intended to be removed to allow placement of the introducer. In a preferred embodiment, a dilator acts as a stiffening means for stiffening the structure of the coronary sinus guiding introducer. The dilator is produced from conventional dilator material and preferably contains a lumen passing therethrough for use with a guidewire. In a preferred embodiment shown in FIGS. 8a, 8b and 8c, the shape of the dilator (400) conforms to the shape of the coronary sinus guiding introducer. By using a dilator with the same shape as the coronary sinus guiding introducer, upon insertion of the dilator into the coronary sinus guiding introducer, support for the overall shape of the coronary sinus guiding introducer is enhanced. By use of these complementary shapes, smooth and effective placement of the coronary sinus guiding introducer into the coronary sinus is possible.

Figures 12A, 12B:
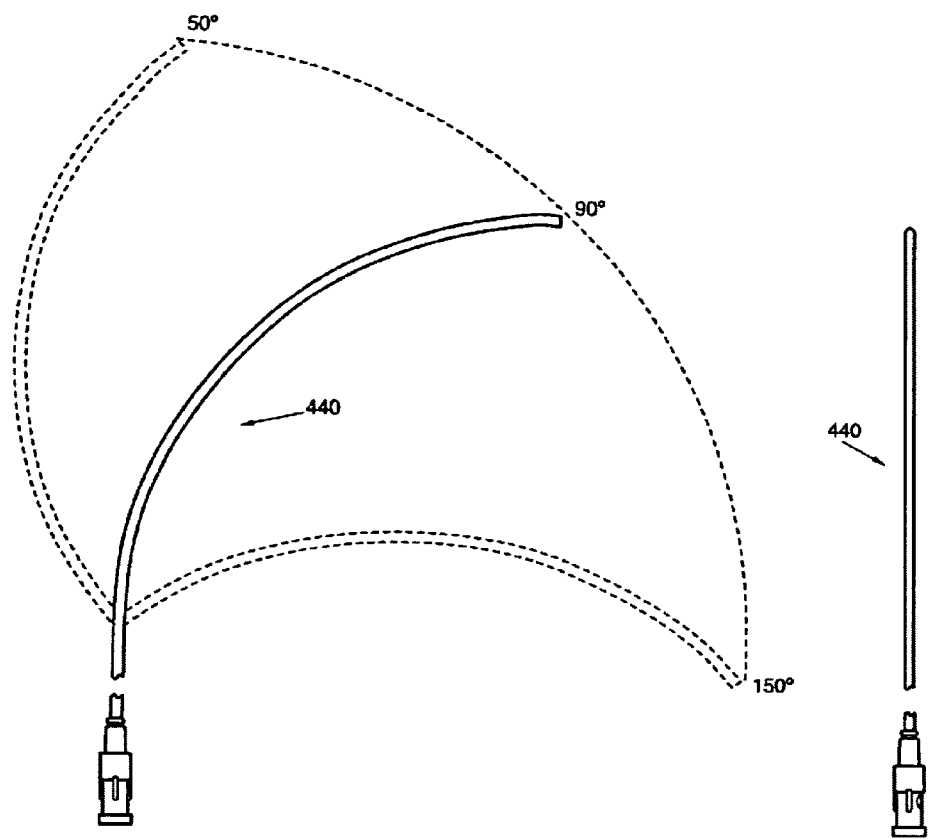

In an alternative embodiment the shape of the introducer (320) and dilator (440) can conform to the gentle curve for the introducer shown in FIG. 5. The shape of a dilator (440) which conforms to this shape is shown in FIGS. 12a and 12b.

Figure 9:
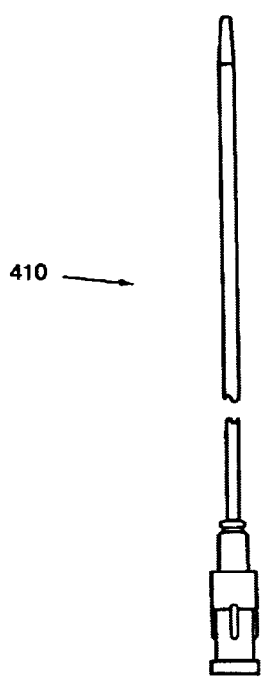
FIG. 9 is a side view of a straight dilator for use with the guiding introducer of FIGS. 2a, 2b and 2c.

If desired in an alternative embodiment, the shape of the dilator (410) can be straight as shown in FIG. 9, such that upon introduction into the lumen of any of the precurved coronary sinus guiding introducer discussed above, the overall shape of the coronary sinus guiding introducer is straightened, making insertion of the combination through the vasculature easier. When the dilator is removed from the lumen of the coronary sinus guiding introducer, the coronary sinus guiding introducer returns to its predetermined shape.

Figures 8A, 8B, 8C:
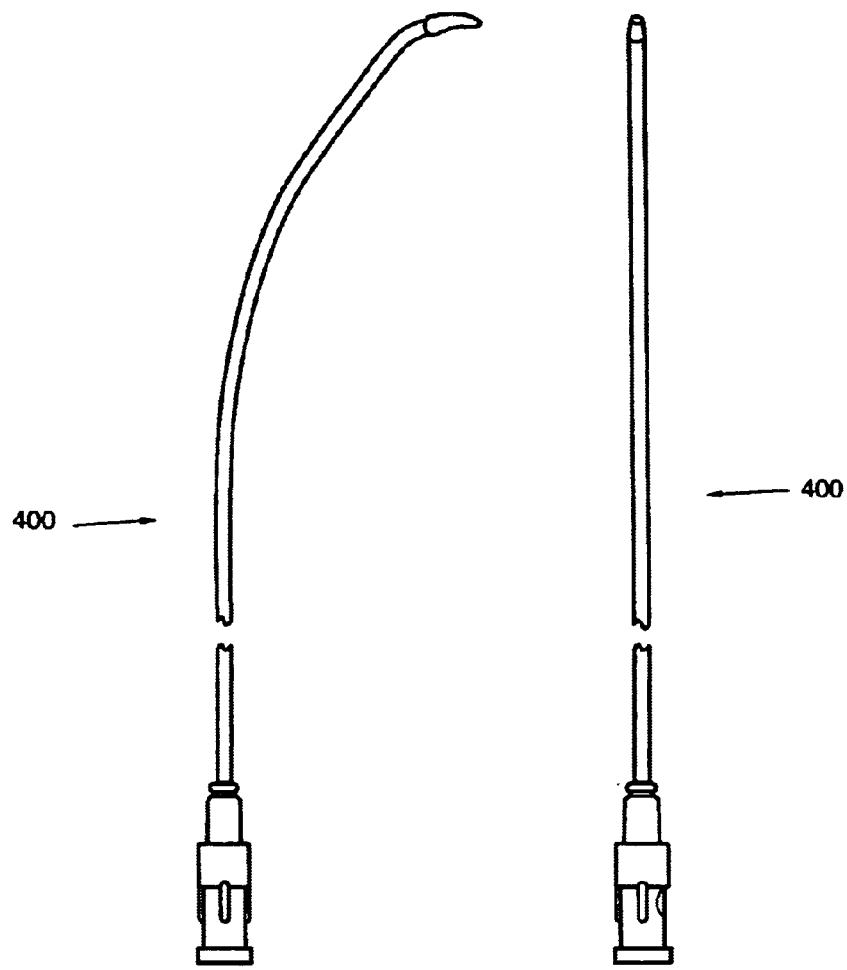
Figure 10:
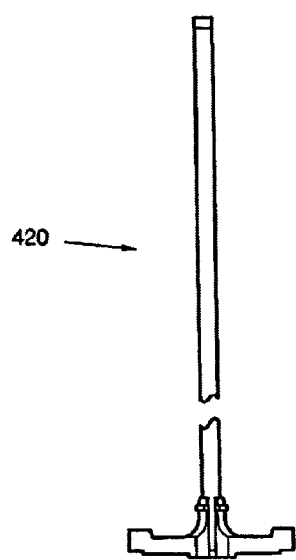
FIG. 10 is a side view of a straight introducer for use with the precurved dilator of FIGS. 8a, 8b and 8c.

In another alternative embodiment, the dilator (400) shown in FIGS. 8a, 8b and 8c can be formed in a fixed curve which is similar to the curvature previously discussed for the coronary sinus guiding introducer and the guiding introducer is a conventional, straight introducer (420) as shown in FIG. 10. When used in combination, the curved dilator and the straight introducer form an overall shape similar, or the same as, the preferred embodiment for the coronary sinus guiding introducer discussed above in the other embodiment.

Using any of these embodiments for a combination of the dilator with the coronary sinus guiding introducer results in a combination device formed in the same preferred shape as that of the coronary sinus guiding introducer above discussed.

Figures 11A, 11B, 11C:
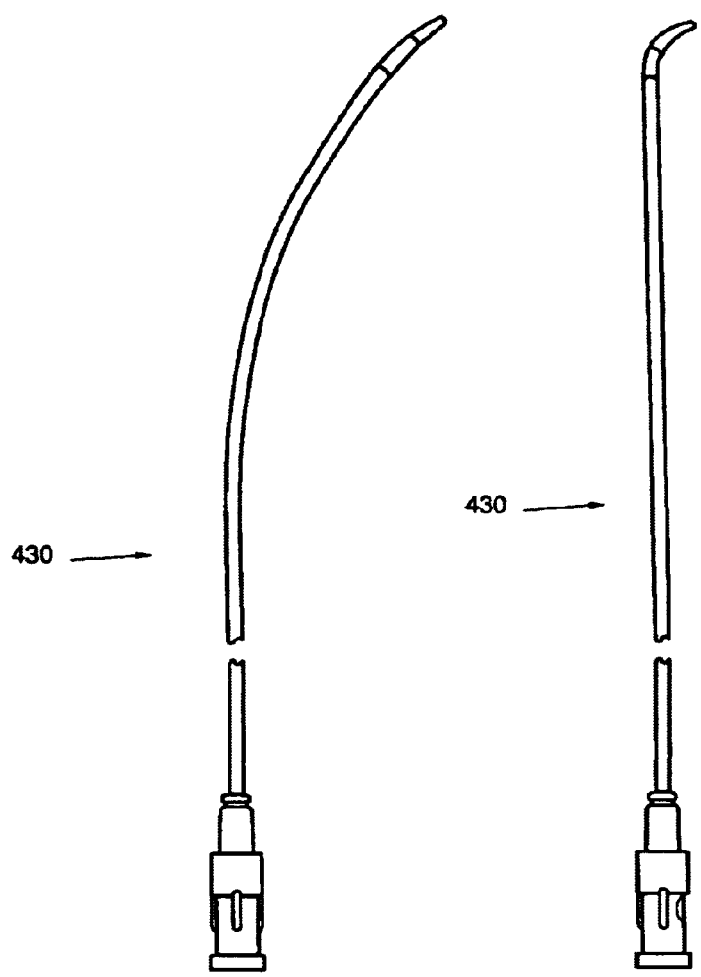

Similar alternative embodiments can also be utilized for dilators and guiding introducers used for the inferior approach to the coronary sinus. For example, in a preferred embodiment, the shape of the dilator (430), as shown in FIGS. 11a, 11b and 11c conforms to the shape of the coronary sinus guiding introducer (340) used for an inferior approach as shown in FIGS. 7a, 7b and 7c. By using a dilator with the same shape as the coronary sinus guiding introducer, upon insertion of the dilator into the coronary sinus guiding introducer, support for the overall shape of the coronary sinus guiding introducer used for an inferior approach is enhanced.

If desired, in an alternative embodiment, the shape of the dilator (410) can be straight as shown in FIG. 9 such that upon introduction into the lumen of the precurved coronary guiding introducer (340) utilized for an inferior approach as shown in FIGS. 7a, 7b and 7c, the overall shape of the coronary sinus guiding introducer utilized for an inferior approach is straightened, making insertion of the combination through the vasculature easier. When the dilator is removed from the lumen of the coronary sinus guiding introducer, the coronary sinus guiding introducer for use in an inferior approach returns to its predetermined shape.

In another alternative embodiment, the dilator (430) can be formed in a fixed curve, such as is shown in FIGS. 11a, 11b and 11c, which curvature is similar to the curvature previously discussed for the coronary sinus guiding introducer for use in an inferior approach and the guiding introducer is a conventional straight introducer (420) as shown in FIG. 10. When used in combination, the curved dilator and the straight introducer form an overall shape similar or the same as the preferred embodiment for the coronary sinus guiding introducer for an inferior approach discussed above in the other embodiments.

In another alternative embodiment, the additional stiffness can be provided to the coronary sinus guiding introducer by means of a precurved, shaped catheter, such as the catheters disclosed in U.S. Pat. Nos. 5,423,772 and 5,549,581.

In operation, a modified Seldinger technique is used for insertion of the coronary sinus guiding introducer and any devices which will pass through the lumen of the guiding introducer into the human body. Once the opening is provided in the vasculature, a guidewire is inserted and advanced through the vasculature into the chamber of the heart where the procedure will be performed. In a preferred embodiment of this invention using the superior approach to the right atrium, the guidewire is advanced through the internal jugular or subclavian vein through the superior vena cava and into the right atrium. The guiding introducer with dilator present in its lumen is then passed over the guidewire into the right atrium as shown in FIG. 1a.

Figure 1B:
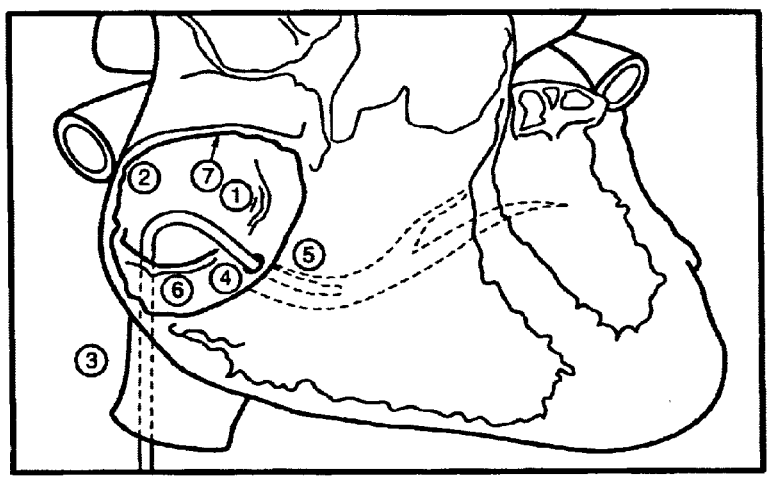
FIG. 1b is a cutaway view of the human heart showing an alternate preferred embodiment of the coronary sinus guiding introducer placed in the coronary sinus using an inferior approach.

When the inferior approach is utilized as shown in FIG. 1b, the guidewire is advanced up through the femoral vein through the inferior vena cava into the right atrium. The coronary sinus guiding introducer with dilator combination is advanced over the guidewire into the right atrium. The guidewire is then removed. The guiding introducer is then advanced under fluoroscopic guidance toward the tricuspid valve with the tip of the guiding introducer pointing medially as shown in FIG. 1b.

The particular structure and curvature of the guiding introducer's distal section permits ease in locating the ostium of the coronary sinus in either the inferior or superior approach. The tip of the coronary sinus guiding introducer is then advanced as far as is required or desired into the coronary sinus. The dilator may be removed from the coronary sinus guiding introducer at any point when appropriate. For example, if the dilator and the coronary sinus guiding introducer both have the same shape as shown, for example, in FIGS. 2a, 2b and 2c and FIGS. 8a, 8b and 8c, it may be best to introduce them in combination into the coronary sinus and only after the coronary sinus guiding introducer is in place will the dilator be withdrawn. This may also be the preferred method of use when the dilator is precurved in the same shape as the preferred guiding introducer as above discussed and when a conventional straight introducer is utilized. Alternatively, if the dilator is straight, it should be withdrawn from the precurved guiding introducer prior to any attempt to place the guiding introducer into the coronary sinus. If the dilator is precurved and the guiding introducer is straight, the introducer is advanced into the coronary sinus once the dilator has been advanced into the coronary sinus.

Once the guiding introducer is in place in the coronary sinus, the medical device to be placed in the patient's heart is then advanced through the lumen of the guiding introducer into the coronary sinus. For example, a temporary or permanent pacemaker lead may be advanced through the lumen of the guiding introducer to be placed within the coronary sinus. A stylet may be inserted into the lumen of the lead to provide additional stiffness for the lead and to allow easy advancement of the lead through the lumen of the coronary sinus guiding introducer. Once the lead has been advanced into the coronary sinus, the stylet is preferably removed. The lead is then secured in place by conventional procedures. After the lead is in position, the guiding introducer is withdrawn from the body of the patient. The order of removal of stylet and introducer and securing the lead in place is not critical and may vary depending on the preference of the medical practitioner. Because the proximal end of the lead is generally either attached to a connector or is directly attached to the pulse generator of the pacemaker, it is often critical that the guiding introducer be splittable to allow it to be split into two lengthwise portions as it is removed from the patient's body. Once it is split, it can be removed from the operating theater. Alternatively, if the lead is relatively small and not connected to a pulse generator and the lumen of the guiding introducer is relatively large, it will not be necessary for the introducer to be splittable.

The guiding introducer can be used to introduce a number of different types of medical instruments into the body through its lumen including a permanent or temporary pacemaker lead, a defibrillator lead, ablation or sensing catheters or any such medical devices that will find use if placed within the coronary sinus. These other uses are well known in the industry and are within the contemplation of the present invention.

The guiding introducer can also be used to introduce a wire guide into the coronary sinus. In this use, the guiding introducer is first advanced into the coronary sinus followed by the guidewire. Once the guidewire is in place, the guiding introducer can be removed. A lead or other types of medical devices can then be advanced over the wire guide until in place in the coronary sinus. In this case the lead, for example, may have a lumen or track so that it can be advanced using the guidewire into the coronary sinus.

While it is apparent from the foregoing that particular forms of the invention have been illustrated and described, various modifications can be made without departing from the spirit and scope of the invention. Accordingly, it is not intended that the invention be limited by this disclosure and all changes which come within the meaning and range of equivalence of the claims are therefore to be embraced therein.

We claim:

1. A process for introducing a medical device into the coronary sinus of a heart of a patient, comprising the steps of:
   (a) introducing a stiffening means into a lumen of a coronary sinus guiding introducer, wherein the guiding introducer contains proximal and distal ends, and wherein the lumen extends from the proximal to the distal end of the guiding introducer,
   (b) introducing the coronary sinus guiding introducer with stiffening means into vasculature of the patient,
   (c) directing the coronary sinus guiding introducer with stiffening means through the vasculature of the patient into a right atrium of the patient's heart,
   (d) introducing a distal tip of the coronary sinus guiding introducer into the coronary sinus of the patient's heart,
   (e) introducing the medical device into the lumen of the coronary sinus guiding introducer,
   (f) advancing the medical device through the lumen of the coronary sinus guiding introducer until it extends away from the distal tip of the coronary sinus guiding introducer into the patient's coronary sinus, and
   (g) withdrawing the stiffening means from the coronary sinus guiding introducer after the introduction of the coronary sinus guiding introducer into the coronary sinus.

2. The process of claim 1 further comprising the steps of removing the coronary sinus guiding introducer from the patient by splitting it into separate, longitudinal portions.

3. The process of claim 1 wherein the coronary sinus guiding introducer comprises an elongated member containing a generally straight proximal section and a precurved, distal section, wherein the precurved, distal section is curved in an arc from about 50 to 150 degrees.

4. The process of claim 3 wherein the precurved distal section comprises first and second curved portions, wherein the first curved portion curves in an arc of about 20 to about 60 degrees, wherein the second curved portion curves in an arc of about 30 to 90 degrees, and wherein the first and second curved portions are substantially coplanar.

5. The process of claim 3 wherein the precurved distal section of the guiding introducer comprises a first curved portion with a first arc and a second curved portion with a second arc, wherein the first curved portion is curved in substantially the same direction as the second curved portion, and wherein the sum of the arcs of the first and second curved portions is about 50 to 150 degrees.

6. The process of claim 5 wherein the sum of the arcs of the first and second curved portions is from about 85 to about 115 degrees.

7. The process of claim 3 wherein the precurved distal section comprises a first and second curved portion, wherein the first curved portion is curved in an arc of about 20 to about 60 degrees, wherein the second curved portion is curved in an arc of about 30 to 90 degrees, and wherein the second curved portion extends out of a plane formed by the first curved portion about 15 to about 90 degrees.

8. The process of claim 3 wherein the precurved distal section comprises a plurality of curved sections and a plurality of straight sections.

9. The process of claim 3 wherein the stiffening means comprises a dilator.

10. The process of claim 1 wherein the medical device comprises an electrophysiological diagnostic device for sensing and/or ablation.

11. The process of claim 1 wherein the stiffening means comprises a dilator.

12. The process of claim 1 wherein the stiffening means comprises a catheter.

13. The process of claim 1 wherein the medical device comprises a pacemaker lead.

14. A process for introducing a medical device into the coronary sinus of a heart of a patient, comprising the steps of:
   (a) introducing a stiffening means into a lumen of a coronary sinus guiding introducer, wherein the guiding introducer contains proximal and distal ends, wherein the stiffening means comprises a dilator, and wherein the dilator comprises a precurved member, wherein the precurved member comprises a first generally straight proximal section and a second precurved, distal section, wherein the precurved, distal section curves through an arc of about 50 to about 150 degrees, and wherein the lumen extends from the proximal to the distal end of the guiding introducer,
   (b) introducing the coronary sinus guiding introducer with stiffening means into vasculature of the patient,
   (c) directing the coronary sinus guiding introducer with stiffening means through the vasculature of the patient into a right atrium of the patient's heart,
   (d) introducing a distal tip of the coronary sinus guiding introducer into the coronary sinus of the patient's heart,
   (e) introducing the medical device into the lumen of the coronary sinus guiding introducer, and
   (f) advancing the medical device through the lumen of the coronary sinus guiding introducer until it extends away from the distal tip of the coronary sinus guiding introducer into the patient's coronary sinus.

15. The process of claim 1 wherein the stiffening means is withdrawn from the coronary sinus guiding introducer prior to introducing the coronary sinus guiding introducer into the coronary sinus.

16. The process of claim 14 wherein the precurved distal section comprises a first and second curved portions wherein the first curved portion is curved in an arc of about 20 to about 60 degrees, wherein the second curved portion is curved in an arc of about 30 to 90 degrees, and wherein the first and second curved portions are substantially coplanar.

17. The process of claim 16 wherein the arc of the first curved portion has a radius of about 2.0 (5.1 cm) to about 5.0 inches (12.7 cm).

18. The process of claim 16 wherein the arc of the second curved portion has a radius of about 0.2 (0.5 cm) to about 2.0 inches (5.1 cm).

19. The process of claim 14 wherein the precurved distal section comprises a plurality of curved sections and a plurality of straight sections.

* * * * *